(12) United States Patent
Gunstream et al.

(10) Patent No.: US 7,875,425 B2
(45) Date of Patent: Jan. 25, 2011

(54) METHODS FOR MONITORING POLYMERASE CHAIN REACTIONS

(75) Inventors: Stephen J. Gunstream, San Francisco, CA (US); Patrick D. Kinney, Hayward, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 916 days.

(21) Appl. No.: 11/270,841

(22) Filed: Nov. 9, 2005

(65) Prior Publication Data

US 2007/0105126 A1    May 10, 2007

(51) Int. Cl.
*C12Q 1/68* (2006.01)
*C12P 19/34* (2006.01)
*C12M 1/34* (2006.01)

(52) U.S. Cl. .................... 435/6; 435/91.2; 435/287.1

(58) Field of Classification Search .................. 435/6, 435/91.2; 536/24.31, 24.32, 24.33, 287.1
See application file for complete search history.

(56) References Cited

U.S. PATENT DOCUMENTS 6,465,241 B2 * 10/2002 Haronian et al. ......... 435/287.2
7,148,043 B2 * 12/2006 Kordunsky et al. ......... 435/91.2
2004/0224317 A1 * 11/2004 Kordunsky et al. ............. 435/6

FOREIGN PATENT DOCUMENTS

| WO | 97/46707 A2 | 12/1997 |
| WO | WO 9746707 A2 * | 12/1997 |
| WO | 01/12854 A2 | 2/2001 |
| WO | 2005/068975 A1 | 7/2005 |

OTHER PUBLICATIONS

International Search Report along with Written Opinion of the International Searching Authority for application No. PCT/US06/60743 dated Nov. 7, 2007.
Fowler et al., "A Multi-Modality Assay Platform for Ultra-High Throughput Screening," Current Pharmaceutical Biotechnology, Bentham Science Publishers, vol. 1, No. 3, pp. 265-281, Jan. 2000.
Supplementary European Search Report for application No. 06850131.1 mailed Nov. 10, 2009.

* cited by examiner

*Primary Examiner*—Suryaprabha Chunduru

(57) ABSTRACT

A method for calibrating temperature can include cycling temperatures of a set of wells, wherein each well of the set comprises a sample with a spectrally distinguishable species. The method can further include measuring a signal from the spectrally distinguishable species for each well at a temperature during a first temperature cycle, and calibrating the temperatures for measuring the signal from each well during subsequent temperature cycles.

19 Claims, 3 Drawing Sheets

METHODS FOR MONITORING POLYMERASE CHAIN REACTIONS

FIELD OF THE DISCLOSURE

The present disclosure relates to devices for monitoring polymerase chain reactions, and more particularly, to methods of calibrating temperature in such devices. The disclosure also relates to methods of reducing the run time of a reaction in such devices.

BACKGROUND OF THE INVENTION

Polymerase chain reaction (PCR) is a process for amplifying quantities of double-stranded deoxyribonucleic acid (DNA). Real-time detection of DNA amplification during the PCR process provides quantitative data for amplifiable DNA target sequences by relating the number of temperature cycles during thermal cycling to reach a concentration threshold (Ct) of the target sequence to the amount of target DNA present at the beginning of the PCR process. In real-time detection, the time required to read a sample during annealing can impact the overall run time. Currently, it takes about 2 hours to run PCR in a standard cycling instrument and about 40 minutes in a fast cycling instrument. In an effort to reduce this time, an excess of enzymes can be added to each well thereby decreasing the reaction time. However, the reaction time can only be decreased to an extent, and the excess enzyme increases the cost of the experiment.

Currently, the 60° C. annealing temperature can be used to take fluorescent reads because it is a stable temperature at which to read spectrally distinguishable species, such as fluorescent dyes. There are chemical and physical limitations to the use of spectrally distinguishable species. One of these limitations is the variation of excitation wavelengths of different colored species. As a result, simultaneously using two or more spectrally distinguishable species with different excitation wavelengths requires multiple excitation light sources. Moreover, the dyes can change in intensity as well as in spectrum with temperature. Because it is not possible to read every well and/or every channel simultaneously, a 20 or 30 second hold exists.

It may be desirable to reduce the time between each cycle by calibrating the temperature of each well thereby reducing the hold time.

SUMMARY OF THE DISCLOSURE

In accordance with exemplary aspects of the disclosure, a method for calibrating temperature can comprise cycling temperatures of a set of wells, wherein each well of the set comprises a sample with a spectrally distinguishable species. The method can further comprise measuring a signal from the spectrally distinguishable species for each well at a temperature during a first temperature cycle; and calibrating the temperatures for measuring the signal from each well during subsequent temperature cycles.

According to some exemplary aspects, a method can comprise measuring a signal from a spectrally distinguishable species present in a first well from a set of wells at a first temperature, heating the set of wells to a second temperature, and measuring a signal from a spectrally distinguishable species present in at least one additional well from the set of wells at the second temperature.

According to various exemplary aspects, a method can comprise measuring a signal from a spectrally distinguishable species present in at least one well at a temperature other than an annealing temperature during a first measurement period, and measuring the same at least one well at the temperature during subsequent measurement periods.

According to some exemplary aspects, a method for reducing the run time of a reaction can comprise cycling a thermal cycler block having a set of wells from about 60° C. to about 95° C. in a linear relationship over a period of time, and measuring a signal from each well in the set of wells.

Some exemplary objects and advantages of the disclosure will be set forth in part in the description which follows and can be learned by practice of the disclosure. The objects and advantages of the disclosure can be realized and attained by means of the elements and combinations particularly pointed out in the appended claims.

It is to be understood that both the foregoing general description and the following detailed description are exemplary and explanatory only and are not restrictive of the disclosure.

The accompanying drawings, which are incorporated in and constitute a part of this specification, illustrate exemplary aspects of the disclosure and, together with the description, serve to explain the principles of the disclosure.

Unless otherwise stated herein, is to be understood that the figures are not necessarily drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

DESCRIPTION OF THE EMBODIMENTS

Reference will now be made in detail to the various aspects of the disclosure, examples of which are illustrated in the accompanying drawings. Wherever possible, the same reference numbers will be used throughout the drawings to refer to the same or like parts.

Figure 1:
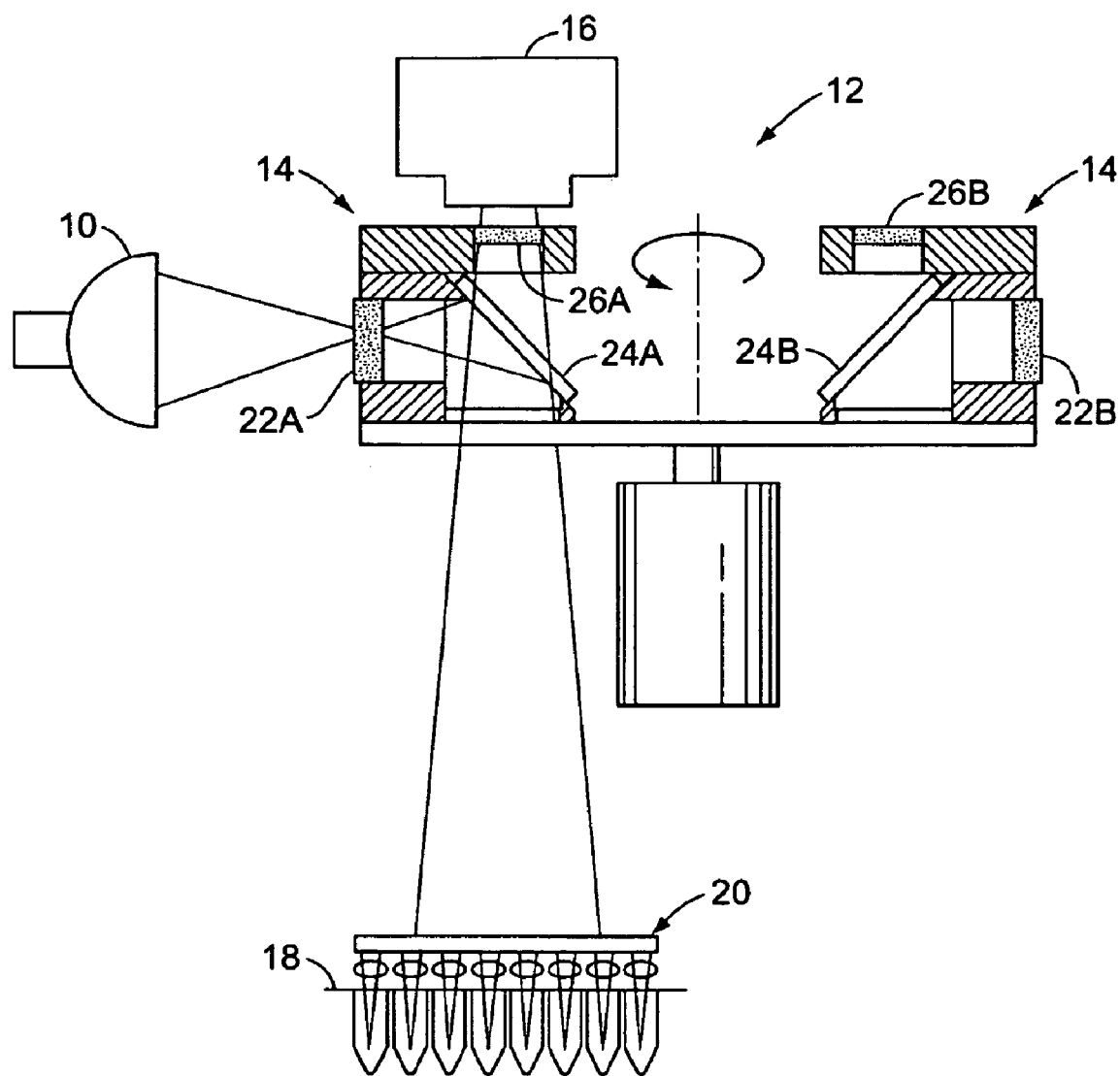
FIG. 1 is a cross-sectional side view of an exemplary detection system in accordance with aspects of the invention.

According to various aspects, FIG. 1 illustrates an exemplary detection system 5. The system can include a light source 10, a filter turret 12 with multiple filter cubes 14, a detector 16, a reaction apparatus 18, and well optics 20. The term "filter" as used herein refers to optical filters in visible or near-visible range such as infra-red, gratings, prisms and other optical components that can be influenced by angle of incidence. Each filter cube 14 can include an excitation filter 22A, 22B, a beam-splitter 24A, 24B, and an emission filter 26A, 26B. These can each be provided to correspond to one of the multiple spectrally distinguishable species, such that species A can correspond to the filter cube 14 with excitation filter 22A, beam-splitter 24A, and emission filter 26A, species B can correspond to the filter cube 14 with excitation filter 22B, beam-splitter 24B, and emission filter 26B, and so on for other species that can be detected from the samples in reaction apparatus 18. The angle of incidence can be unique for each well of the reaction apparatus 18 because each well's specific location can be unique relative to the optical filter. Accordingly, all calculations and filter coefficients can be unique per sample well. It will be apparent to one skilled in the art that other systems for detection with different components, for example without a filter turret, can benefit from the present teachings.

The detector 16 can be utilized with or incorporated into a reaction apparatus 18 that replicates ("amplifies") selected portions of DNA by, for example, PCR. The term "detector" as used herein can refer to a charge coupled device (CCD), a charge induction device (CID), an array of photomultiplier tubes (PMT), photodiode, CMOS device, or other means of detecting fluorescent light emitted from multiple spectrally distinguishable species in a sample. The detector can include an external computer or internal processor that provides calculation to determine correction factors.

The reaction apparatus 18 can be conventional and should function without interference from the instrument that monitors the amount of DNA in real time during replication. Suitable reaction apparatuses are described, for example, in U.S. Pat. Nos. 5,475,610 and 5,656,493, the disclosures of which are hereby incorporated by reference.

Figure 2:
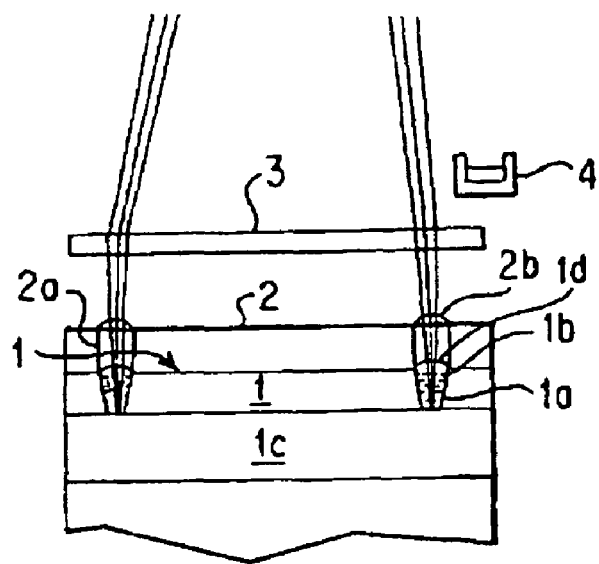
FIG. 2 is a side view of an exemplary reaction apparatus in accordance with aspects of the invention.

As shown in FIG. 2, the reaction apparatus 18 can comprise two main components, namely a thermal cycler block 1 with at least one well 1$a$, for example, for holding at least one vial 1$b$ containing a sample, and a thermal cycle controller 1$c$.

To facilitate heating or cooling, the thermal cycler block 1 can be formed of a material that has high thermal conductivity, such as copper, aluminum, or silicon. The thermal cycler block 1 can comprise at least one layer. According to some aspects, a first layer can be formed from a material having moderate or low thermal conductivity, while a second layer can be provided as a thin layer, such that the temperature of the at least one well can be conveniently controlled by heating or cooling the device through second layer, regardless of the thermal conductivity of the first layer. In some aspects, the second layer can be provided in the form of an adhesive copper-backed tape. In some aspects, the block can be heated and/or cooled by electrical means, liquid or air coolant, or a combination of these or other means.

The thermal cycle controller 1$c$ can regulate the temperatures of the at least one well 1$a$, for example, by providing temperature control from about 0° C to about 100° C. In an embodiment, the thermal cycle controller 1$c$ can include a conductive heating element (not shown) for each well 1$a$, configured to rapidly heat the contents of the well to a selected temperature. The thermal cycle controller 1$c$ can be adapted to regulate the temperatures of the wells by, for example, heating and cooling the wells in accordance with a selected assay protocol, for example, by cycling the temperature of the thermal cycler block 1 through a specified temperature program.

A sample, such as an aqueous suspension of biological material, can comprise a "seed" sample of DNA, selected DNA primer strands, DNA elements, enzymes, and other chemicals. The sample also can comprise a spectrally distinguishable species, such as a fluorescent dye, that signals proportionately and more strongly in the presence of double stranded DNA. The term "spectrally distinguishable species" as used herein refers to dyes, reporters, or reagents such as FAM, SYBR Green, VIC, JOE, TAMRA, NED, CY-3, Texas Red, CY-5, ROX (passive reference), etc. In an embodiment, fluorescent dye labeled "probes", which are DNA-like structures with complimentary sequences to selected DNA strand portions, can also be used. Other dyes that have similar characteristics can be utilized. As used herein, the term "marker dye" refers to the type that binds to double stranded DNA, or to the probe type, or to any other type of dye that attaches to DNA so as to fluoresce in proportion to the quantity of DNA. A sample can also contain an additional, passive dye (independent of the DNA) to serve as a reference.

The sample in the at least one vial can be cycled through temperature phases so as to affect a polymerase chain reaction. One phase can be a lower temperature extension phase of the PCR reaction at about 60° C., which is the phase where all of the DNA strands have recombined into double strands. A second phase can be a higher temperature denaturing phase at about 95° C., during which the DNA is denatured or split into single strands.

The at least one vial 1$b$ for use in the reaction apparatus 18 can be any size or form. In some aspects, the at least one vial 1$b$ can be formed conically in a plastic unitary tray containing a plurality of vials, for example 96 vials in an array of 12 by 8. The tray can be removable from the block for preparations. A plastic unitary cover with caps 1$d$ for the vials can rest or attach over the vials to prevent contamination and evaporation loss. Other means can be used for this function, such as oil on the sample surface, in which case, caps are not needed. If used, the caps can be transparent to light utilized in the instrument, and can be convex facing upwardly.

A platen 2 can rest over the vial caps or, if none, directly over the vials. The platen, such as aluminum, can have an array of holes 2$a$ therethrough aligned with the vials, each hole having a diameter about the same as the vial top diameter. If there are caps, the platen should have its temperature maintained by a film heater or other means for heating the platen sufficiently to prevent condensation under the caps without interfering with DNA replication in the vials, for example holding the platen at a slightly higher temperature than the highest sample temperature than the thermal cycler reaches.

Above each of the vials can be a lens 2$b$ positioned for its focal point to be approximately centered in the sample in the vial. Above this lens is a field lens 3 configured to provide a telecentric optical system. The field lens 3 can be an aspherically corrected Fresnel lens for minimal distortion. A neutral density pattern (not shown) to correct nonuniformities in illumination and imaging can be mounted on or in proximity to the field lens 3, for example, to attenuate light in the center of the image field. A folding optical mirror (not shown) can be optionally mounted at 45°. This can be omitted, or other such folding optics can be used. Also the field lens and/or the vial lenses each can comprise at least two lenses that effect the required focusing. The word "lens" herein includes such multiplicities.

Figure 3:
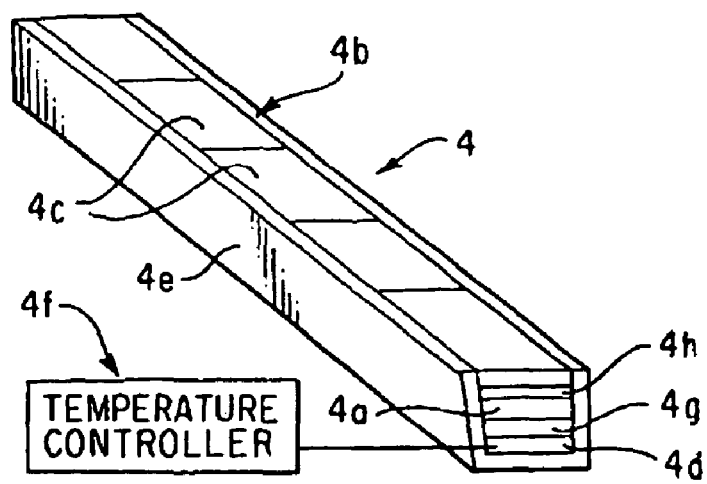
FIG. 3 is a front perspective view of an exemplary fluorescent reference member in accordance with aspects of the invention.

According to various aspects, the system can include a fluorescent reference member 4 that can emit reference light in response to an excitation beam. The reference member 4 can be formed of a plurality of reference emitters, e.g. six, each emitting a reference beam of different intensity in response to an excitation beam. The range of these intensities can approximate the range of intensities expected from the spectrally distinguishable species in the vials. For example, each segment can be separated in brightness by about a factor of about 2.5. Referring now to FIG. 3, in some aspects, the reference member 4 can comprise a plastic fluorescent strip 4a and a neutral density filter 4b mounted over the fluorescent strip 4a, optionally with an air space 4h between, such that a portion of the excitation beam and the reference beam are attenuated by the neutral density filter. The neutral density filter can have a series of densities 4c to affect the plurality of reference emitters (segments) each emitting a reference beam of different intensity. A heating strip 4d and an aluminum strip 4g configured to smooth the heating can be mounted in a trough 4e on the bottom thereof, and the fluorescent strip 4a can be mounted on the aluminum strip over the heating strip. To prevent heat loss, this assembly can be covered by a transparent plexiglass window (not shown, so as to display the varying density filter). To help maintain constant fluorescence, the heating strip 4d can be controlled to maintain the fluorescent strip 4a at a constant temperature against the thermal cycles of the cycler block 1 and other effects. This can be done because most fluorescent materials change in fluorescence inversely with temperature.

According to various aspects, a reaction apparatus 18 can comprise a set of wells, wherein each well of the set comprises a sample with a spectrally distinguishable species. The sample can be the same or different in each well of the set. Likewise, the spectrally distinguishable species can be the same or different in each well of the set.

Figure 4A:
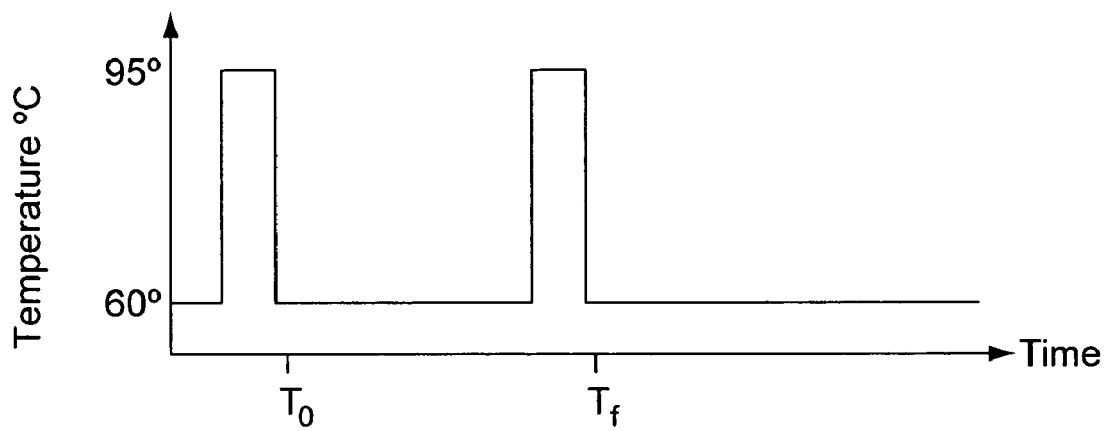
FIG. 4A is a graph of time versus temperature and exemplifies an embodiment of a method disclosed herein.

As shown in FIG. 4A, a "cycle" can begin at a time, for example, $T_o$, and can end with a final time $T_f$. The period of time for a cycle to complete can vary depending on a number of factors including, but not limited to, the number of wells in the set, for example 96; the time required to position each well of the set under the detector 16; the time required to detect and measure a signal from the spectrally distinguishable species in each well; the time required to move from one well to the next well; and the time for a reaction in a well to occur. According to some aspects, the run time of a reaction can be reduced by calibrating the temperature of each well at the same time that the signal from the spectrally distinguishable species is measured. This temperature calibration can reduce the run time of the reaction while not affecting the data integrity.

In an aspect, the period of time between measuring a signal from a first well to a second well can be less than about 30 seconds, for example less than about 20 seconds, and as a further example, less than about 5 seconds. Once a signal from each well of the set has been measured then another cycle can begin.

Moreover, over the course of the cycle, the temperature can increase and/or decrease. As shown in FIG. 4A, each well of the set can have the same temperature, such as 60° C., when the signal from the spectrally distinguishable species is measured in a first cycle. After the signal from each well has been measured, the temperature can be increased to, for example, a denaturing temperature, and then decreased. However, for each subsequent cycle, the signal from each well of the set can be read at the same temperature as in the first cycle. For example, if all of the wells during a first cycle are at about 60° C., then all of the well should be at about 60° C. for each subsequent cycle when the signals are read so that the data is not compromised.

Figure 4B:
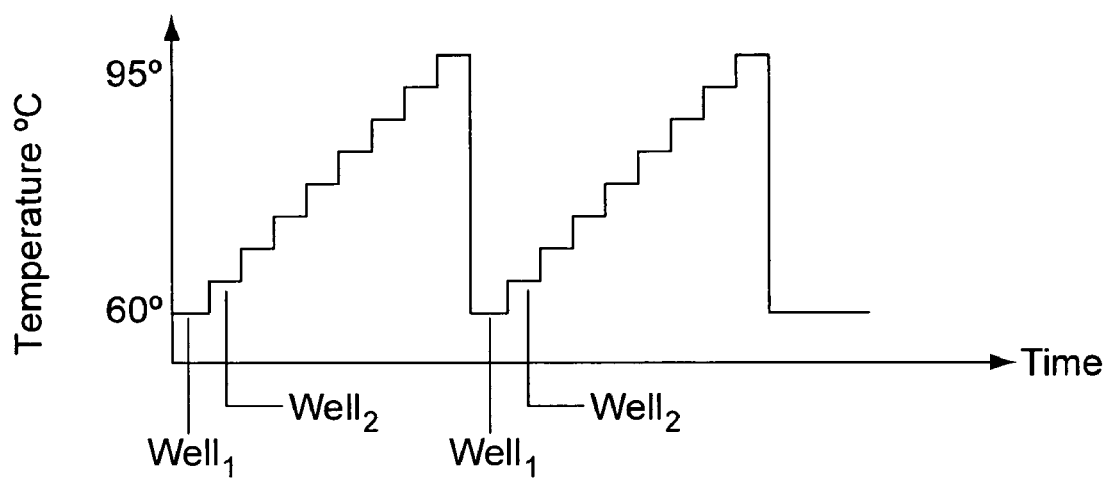
FIG. 4B is a graph of time versus temperature and exemplifies an embodiment of a method disclosed herein.
Figure 4C:
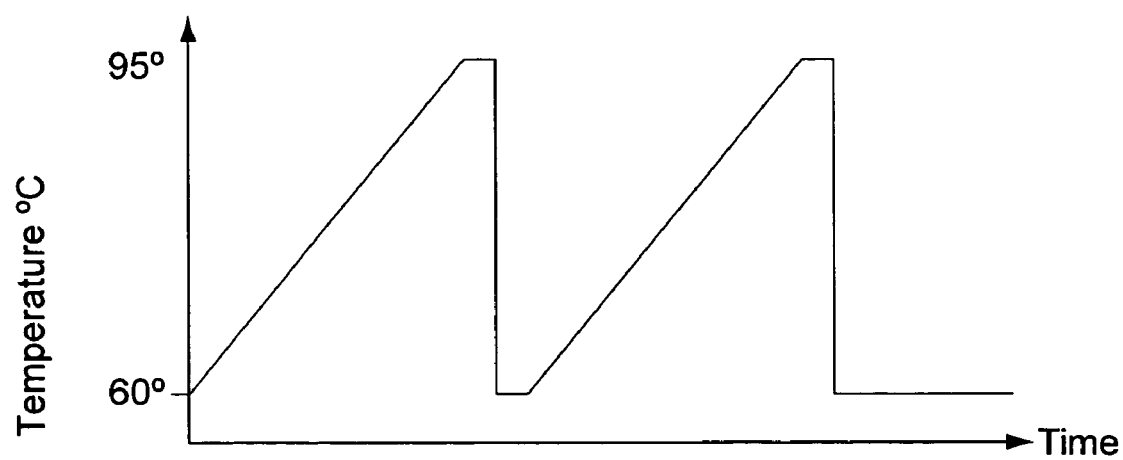
FIG. 4C is a graph of time versus temperature and exemplifies an embodiment of a method disclosed herein.

In various aspects, as shown in FIG. 4B, for example, well #1 of the set can have a first temperature when its signal is measured. The first temperature can be greater than or equal to an annealing temperature of DNA. The temperature of the thermal cycler block 1 can be slowly increased, and optionally held for a period of time, so that well #2 of the set has a higher temperature when its signal is measured as compared to well #1. In another embodiment, the temperature can be slowly increased in a linear relationship over time, for example, so that one temperature is not held for a period of time, as shown in FIG. 4C. In some aspects, the temperature can range from about 60° C. to about 95° C. over the course of a cycle. For example, well #1 can have a temperature of about 60° C. and well #2 can have a temperature of about 61° C. during a first cycle. For each subsequent cycle, the temperature of the thermal cycler block can be calibrated so that well #1 again has a temperature of about 60° C. and well #2 can have a temperature of about 61° C. The particular temperature of each well is not important for the first cycle, so long as during each subsequent cycle the temperature of each well is substantially the same as it was during the first cycle.

In an aspect, at least one spectrally distinguishable species can be present in at least one well. Spectral deconvolution can be used to increase the number of spectrally distinguishable species that can be simultaneously distinguished. Running multiple spectrally distinguishable species and reading their signals at different temperatures can allow for better spectral separation and/or more degrees of freedom for spectral deconvolution. This can be possible because each species responds to temperature changes differently. In various aspects, the same filters can be read at multiple temperatures thereby generating equations for spectral separation.

In various aspects, the signal of the spectrally distinguishable species can be read at any temperature, whether stable or increasing. This can occur by performing the spectral calibration in the same state as reading. For example, the spectral calibration can be performed similarly to the run time reading in order to avoid a loss in spectral deconvolution. In an aspect, each species spectra can be calibrated as a function of temperature to calculate a virtual signal at any temperature.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "a well" includes two or more different wells. As used herein, the term "include" and its grammatical variants are intended to be non-limiting, such that recitation of items in a list is not to the exclusion of other like items that can be substituted or added to the listed items.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A method of calibrating temperature comprising:
cycling temperatures of a set of wells; said cycling including a change in temperature that is substantially linear for at least a portion of time for each cycle; wherein each well of the set comprises a sample with a spectrally distinguishable species;

staggering the measurement of a signal from the wells, wherein the measurements are initiated successively during the substantially linear portion of a first temperature cycle; and measuring the signal from each well during subsequent temperature cycles initiated at about the same temperature for each well.

2. The method of claim 1, wherein the temperature cycles range from about 60° C. to about 95° C.

3. The method of claim 1, wherein the spectrally distinguishable species is selected from the group consisting of dyes, reporters, and reagents.

4. The method of claim 1, wherein the spectrally distinguishable species is selected from the group consisting of FAM, SYBR Green, VIC, JOE, TAMRA, NED, CY-3, Texas Red, CY-5, and ROX.

5. The method of claim 1, wherein the temperature from the spectrally distinguishable species for each well is different during the first temperature cycle.

6. The method of claim 1, wherein the temperature from the spectrally distinguishable species for each well is the same during the first temperature cycle.

7. A method comprising:
cycling temperatures of a set of wells, wherein a temperature change is substantially linear for at least a portion of time for each cycle;

measuring a signal from a spectrally distinguishable species present in a first well from the set of wells at a first temperature during the cycling;

measuring a signal from a spectrally distinguishable species present in at least one additional well from the set of wells at a second temperature during the substantially linear portion of the cycling.

8. The method of claim 7, wherein the first temperature is greater than or equal to an annealing temperature of DNA.

9. The method of claim 7, wherein the first temperature is greater than or equal to about 60° C.

10. The method of claim 7, wherein less than about 30 seconds elapse between measurements.

11. The method of claim 7, wherein less than about 20 seconds elapse between measurements.

12. The method of claim 7, wherein the second temperature is held for a period of time.

13. The method of claim 12, wherein the period of time is less than about five seconds.

14. The method of claim 7, wherein the second temperature is not held for a period of time.

15. A method comprising:
cycling a thermal cycler block having a set of wells from about 60° C. to about 95° C. in a substantially linear ramp over a period of time measuring a signal from a spectrally distinguishable species present in at least one well at a temperature other than an annealing temperature during a first measurement period on the linear ramp; and measuring a signal from the same at least one well at the temperature during subsequent measurement periods.

16. The method of claim 15, wherein a first measurement period comprises heating the at least one well and cooling the at least one well.

17. The method of claim 15, wherein the signal from the at least one well is measured in less than about 30 seconds.

18. The method of claim 15, wherein the signal from the at least one well is measured in less than about 20 seconds.

19. The method of claim 15, wherein the at least one well from the set of wells comprises a spectrally distinguishable species.

* * * * *